(12) United States Patent
Ragaru et al.

(10) Patent No.: US 8,137,450 B2
(45) Date of Patent: Mar. 20, 2012

(54) COLLAGEN-BASED LYOPHILISED GLUE AND THE USE THEREOF FOR PRODUCING AN ADHESIVE PROSTHESIS

(75) Inventors: Bernard Ragaru, Brignais (FR); Benjamin Herbage, Lyons (FR)

(73) Assignee: Symatese, Chaponost (FR)

( * ) Notice: Subject to any disclaimer, the term of this patent is extended or adjusted under 35 U.S.C. 154(b) by 749 days.

(21) Appl. No.: 11/570,979

(22) PCT Filed: Jul. 7, 2005

(86) PCT No.: PCT/FR2005/050550
§ 371 (c)(1),
(2), (4) Date: Dec. 20, 2006

(87) PCT Pub. No.: WO2006/005890
PCT Pub. Date: Jan. 19, 2006

(65) Prior Publication Data
US 2008/0295735 A1 Dec. 4, 2008

(30) Foreign Application Priority Data

Jul. 8, 2004 (FR) .................................... 04 07644
Jul. 8, 2004 (FR) .................................... 04 07646

(51) Int. Cl.
*C09J 189/00* (2006.01)
(52) U.S. Cl. ...................................... 106/124.4; 602/52
(58) Field of Classification Search .................. None
See application file for complete search history.

(56) References Cited

U.S. PATENT DOCUMENTS

| 4,280,954 A | * | 7/1981 | Yannas et al. ............... 530/356 |
| 4,362,567 A | | 12/1982 | Schwarz et al. |
| 4,623,553 A | * | 11/1986 | Ries et al. .................. 427/2.27 |
| 4,650,678 A | | 3/1987 | Fuhge et al. |
| 5,171,273 A | * | 12/1992 | Silver et al. ............... 623/13.11 |
| 5,385,606 A | | 1/1995 | Kowanko et al. |
| 5,876,444 A | * | 3/1999 | Lai ............................... 424/423 |
| 5,972,385 A | * | 10/1999 | Liu et al. ...................... 424/486 |
| 6,165,488 A | * | 12/2000 | Tardy et al. ................. 424/426 |
| 6,309,670 B1 | * | 10/2001 | Heidaran et al. ............ 424/486 |
| 6,630,457 B1 | * | 10/2003 | Aeschlimann et al. ......... 514/54 |
| 6,706,684 B1 | * | 3/2004 | Bayon et al. .................... 514/2 |
| 6,969,523 B1 | * | 11/2005 | Mattern et al. ............... 424/423 |
| 2005/0004217 A1 | * | 1/2005 | Yamamoto et al. .......... 514/559 |

FOREIGN PATENT DOCUMENTS

| EP | 0913162 A1 | | 5/1999 |
| WO | WO98/15299 | | 4/1998 |
| WO | WO98/31403 | | 7/1998 |
| WO | WO0105443 | | 1/2001 |
| WO | WO02/36147 | | 5/2002 |
| WO | WO0236147 | * | 5/2002 |

OTHER PUBLICATIONS

Teramachi et al, porous type tracheal prothesis sealed with collagen, 1997, Ann Thorac Surg, vol. 64, pp. 965-969.*

* cited by examiner

*Primary Examiner* — Melvin Mayes
*Assistant Examiner* — Stefanie Cohen
(74) *Attorney, Agent, or Firm* — Heslin Rothenberg Farley & Mesiti P.C.; Andrew K. Gonsalves

(57) ABSTRACT

A lyophilized glue contains a collagen which is partially crosslinked with the aid of at least one type of aldehyde. A method for preparing the glue and the use thereof for producing an adhesive on anti-adhesive prosthesis are also provided.

29 Claims, 2 Drawing Sheets

Figure 1:
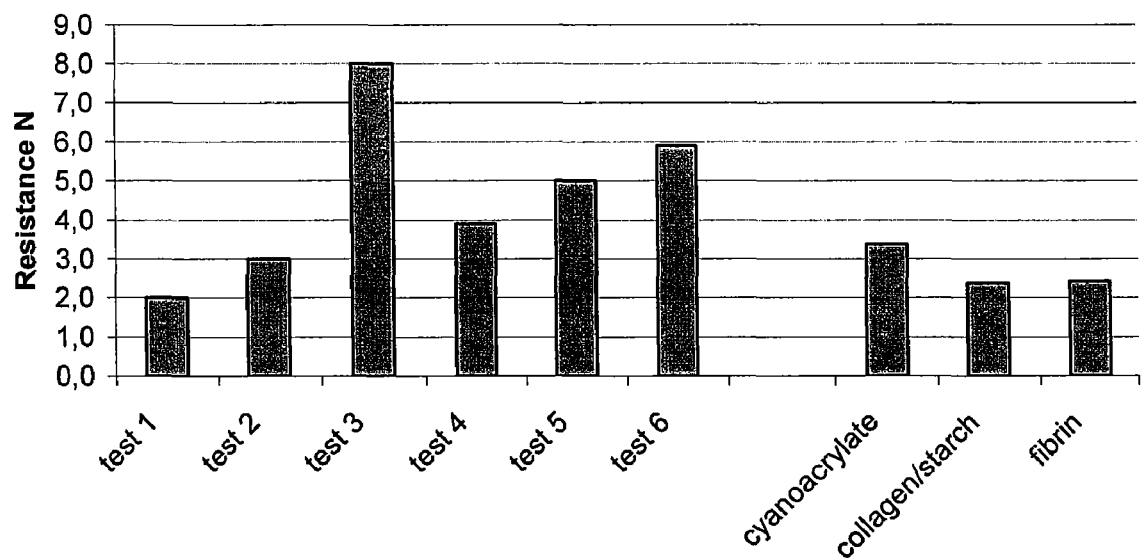

Bond strength (muscle model) at 20 hours

COLLAGEN-BASED LYOPHILISED GLUE AND THE USE THEREOF FOR PRODUCING AN ADHESIVE PROSTHESIS

CROSS REFERENCE TO RELATED APPLICATIONS

This is a Section 371 filing of international application No. PCT/FR2005/050550 filed on Jul. 7, 2005, and published, in French, as International Publication No. WO 2006/005890 A1 on Jan. 19, 2006, and claims priority of French Application No. 0407644 filed on Jul. 8, 2004 and French Application No. 0407646 filed on Jul. 8, 2004, which applications are hereby incorporated by reference herein, in their entirety.

BACKGROUND ART

This invention lies in the field of glues designed for surgical or therapeutic use.

More precisely, this invention deals with a glue comprising a mixture of collagen and a crosslinking agent of the aldehyde type or a modified collagen with aldehyde functions and presented in lyophilised form. It also concerns a process for preparing such glue, its applications, the combination of this glue with a prosthetic material to obtain adhesive prostheses and the method for preparing said prostheses.

This glue is particularly suited to gluing two biological tissues together or to glue a prosthesis onto a biological tissue. It can also be applied directly to a biological tissue. In this latter case, it may notably be used as a local haemostatic device or a support for sustained-release drugs.

There are essentially two types of biological glues in the market: fibrin-based glues and collagen-based glues.

Fibrin-based glues, such as Tissucol, have been used since the 1970s. These glues contain a fibrinogen whose polymerisation is induced by a thrombin solution in the presence of factor XIII and fibronectin. This polymerisation leads to the formation of a fibrin clot that forms the bond. In fact, the aim is to recreate a coagulation phenomenon in situ. The problem related to these glues lies in the use of products made with human plasma, with the risks of contamination by viruses or related non-conventional transmissible agents.

Collagen is particularly well suited for use in glue as this biomaterial, capable of solidifying and then being reabsorbed, is biocompatible. Collagen as such, however, has weak adhesive power.

Thus, a composition based on collagen, resorcinol and formaldehyde was developed in the 1960s (GRF glue or French glue). Resorcinol is combined with formaldehyde to obtain collagen crosslinking and the formation of a solid polymer network. Problems of toxicity have been observed, mainly linked to the addition of formaldehyde (Braunwald et al., Surgery, 59: 1024-1030 (1966); Bachet et al., J Thorac. Cardiovasc. Surg., 83: 212-217 (1982)).

Document EP 0 862 468 describes the use of a macromolecular polyaldehyde, such as oxidized starch, for the crosslinking of a collagenic constituent in the context of biodegradable biological glues. It has been demonstrated that the mixture of such an aldehyde with a collagenic constituent, both in an aqueous solution or rehydrated after lyophilisation, is able to form an adhesive crosslinked material with no phenomenon of aldehyde diffusion.

In practice, however, it has been seen that the required system is complex and delicate to handle for the user. It requires:

means of storage and availability of two distinct compositions,
  supply of these compositions in heated syringes,
  their extemporaneous mixture using a specific system,
  application of the mixture, as quickly as possible, on the wound to be treated.

The result is that this type of glue is not practical to use.

Document EP 0 913 162 foresees the application of a support combined with collagen, for example a glutaraldehyde crosslinked bovine collagen, for the treatment of hernias. In this document, the bond is obtained by applying energy and pressure, the energy having the effect of creating free ends on the collagen fibres and the pressure or force creating new bonds between these ends and the polymer chains of the other surfaces involved.

In this last case, the product is directly ready for use and its storage is made easier. Obtaining the bonding effect, however, depends on the practitioner's application of a source of energy. This step requires the presence of a specific material and highly complicates the operating technique. In the end, it is not of great interest in terms of cost and time compared with the conventional fastening techniques (staples and sutures).

There is therefore an obvious need for biological glues and derived prostheses that are easy to prepare, store, transport and apply.

SUMMARY OF THE INVENTION

Thus, the Applicant has developed a product obtained by the lyophilisation of a mixture of collagen and an aldehyde, or of collagen with aldehyde functions, and which has very interesting bonding properties.

In a first embodiment, the glue thus obtained is solely constituted of collagen and the crosslinking agent with at least one aldehyde function of collagen that is modified so as to present at least one aldehyde function.

It is, however, possible to envisage adding other constituents to the collagen/aldehyde mixture, such as additives increasing the wetting power of the glue. These additives may be sugar polymers (dextrin and starch), for example.

Advantageously, the glue according to the invention also contains elements capable of polymerising with the aldehyde to increase crosslinking, such as phenols, and more particularly resorcinol.

These additives can advantageously be added before lyophilisation.

By "collagen" is meant native collagen that is partially denatured or even totally denatured (gelatine). This notably includes type I and/or III collagen, of animal origin (bovine, for example), fibrous or pepsinated. The collagen then comes in the form of a suspension or solution (also called gel), respectively, depending on the solubility of said collagen.

Crosslinking can, a priori, be achieved with any molecule with at least one aldehyde function able to react with the collagen.

According to the present invention, small molecules, such as glutaraldehyde, play the role of a crosslinking agent and for this are mixed with the collagen.

In the biological context, it may be advantageous for the crosslinking agent to have sufficient molecular weight to avoid phenomena of diffusion after its salting out of the complex with the collagen inevitably taking place in vivo.

The crosslinking agent may therefore alternatively be a biodegradable macromolecular polyaldehyde oxidized polysaccharide or mucopolysaccharide of natural origin, such as starch, dextran, agarose, cellulose, chitosan, alginic acid, glycosaminoglycans, hyaluronic acid, chondroitin sulphate or their derivatives.

According to the invention, a biodegradable macromolecular polyaldehyde of natural origin such as oxidized starch may advantageously be used.

Alternatively, the aldehyde functions are provided by the collagen itself. To this aim, the collagen is modified to create aldehyde functions. There are different protocols for modifying collagen so that it presents at least one aldehyde function.

In a first case, the aldehyde functions are inserted into the collagen either by grafting said functions or by enzyme reaction. In both cases, only the lysine residues in the collagen are modified to create aldehyde functions.

Alternatively, and according to a second embodiment of the invention, the collagen is modified by oxidative cleavage, as described in document FR 2 715 309, which leads to the creation of aldehyde functions both in the lysine residues and in the sugars of the collagen.

Advantageously, a collagen acid solution is incubated at ambient temperature, in the presence of a periodic acid solution, or one of its salts, at a concentration between 1 and $10^{-5}$ M.

In practice, such a glue is prepared by mixing solutions (or suspensions) of collagen on the one hand and aldehyde on the other. The mixture is made at an acid pH, notably at a pH between 3 and 5.5, so that crosslinking does not take place or is incomplete. Suitably, 5 to 2,000 µmol of aldehyde function are added per gram of collagen.

Likewise, when the collagen itself is used as the source of the aldehyde functions, it is modified so as to create 5 to 2,000 µmol of aldehyde function per gram of collagen and is maintained at a pH between 3 and 5.5.

By "incomplete crosslinking of the collagen" is meant the fact that free aldehyde functions remain that are ready to react in situ. They will react once the pH conditions become favourable again through the buffering action of body fluids.

Then, the mixture of collagen/aldehyde and/or modified collagen in solution undergoes lyophilisation. Lyophilisation is characterised by vacuum drying of the frozen mixture. In the context of the invention, lyophilisation provides many advantages. It notably stops the incomplete crosslinking reaction, thus stabilising the product before use. This stability in dry form at ambient temperature is a notable improvement over biological glues which conventionally have to be stored at 4° C. The product obtained is rich in collagen compared with products in solution, which are limited by their excessive viscosity. In lyophilised form, the product notably has the advantage of being easy to handle by the practitioner, compared with liquid formulations. It is thus possible to use the lyophilised glue by coelioscopy.

For clinical applications, the lyophilised collagen is then sterilised. Sterilisation is the last step in preparing the glue or prostheses according to the invention. It can be done using physical agents, such as ionising rays (notably β or γ), or a chemical agent, such as ethylene oxide or hydrogen peroxide.

This process of preparation results in a glue in the form of a lyophilisate that is solid and easy to handle. Such a glue can then be conditioned in the form of a sponge or powder. Its adhesive effect develops fully once the glue is inserted into the human body, with physiological conditions reinforcing collagen crosslinking by solubilisation and pH augmentation.

Moreover, this preparation has the advantage of combining adhesive power and haemostatic power. Unlike gelatine-based glues, collagen, by preserving its structure, encourages coagulation. This glue is thus perfectly suited to gluing biological tissues together.

Alternatively, a glue according to the invention may be combined with a prosthetic material to ensure its bond to the biological tissue. The prosthetic materials generally have a strengthening role and are, for example, constituted of a woven (polyester fibres, for example), non-woven, knitted or polypropylene network. Preferably, the prosthetic material is a polyester, polypropylene or cellulose lattice.

The invention also concerns a privileged method for preparing such an adhesive lyophilised prosthesis.

According to this embodiment, the prosthetic material is immersed in the solution (or suspension) obtained by mixing the collagen with the crosslinking agent and/or containing the collagen with the aldehyde functions. In other words, said preparation is poured onto the prosthetic material.

The privileged embodiments concerning the mixture of collagen with the crosslinking agent and/or modified collagen with the aldehyde functions are the same as those described above in relation to the lyophilised glue, notably concerning the crosslinking agents used, the collagen modification protocols and the presence of additives.

The whole then undergoes lyophilisation. This gives rise to an intimate combination of the material and the glue. Here again, in the therapeutic or surgical context, it is necessary to sterilise the prosthesis according to the aforementioned protocols.

This glue can, for example, be used during operations in visceral and parietal surgery in which it is necessary to fasten the prosthesis to tissue. Then, the prosthetic reinforcement undergoes cell recolonisation and tissue integration, for example for treating eventrations or hernias.

Moreover, an anti-adherent effect can be created on one surface of the prosthesis thus obtained, by pouring on, before sterilisation, a functionalised hyaluronic acid gel (with nitrogen, amide, dihydrazid functions, etc.) and crosslinked (with oxidized starch, for example). After coating and drying, and before sterilisation, the product obtained may once again undergo lyophilisation and/or baking to additionally structure the film. In the end, a prosthesis with one surface coated with functionalised, crosslinked hyaluronic acid is obtained.

BRIEF DESCRIPTION OF THE DRAWING FIGURES

The invention and its resulting advantages can be better understood from the following description of an embodiment and the appended figures. These are in no way restrictive, however.

Figure 2:
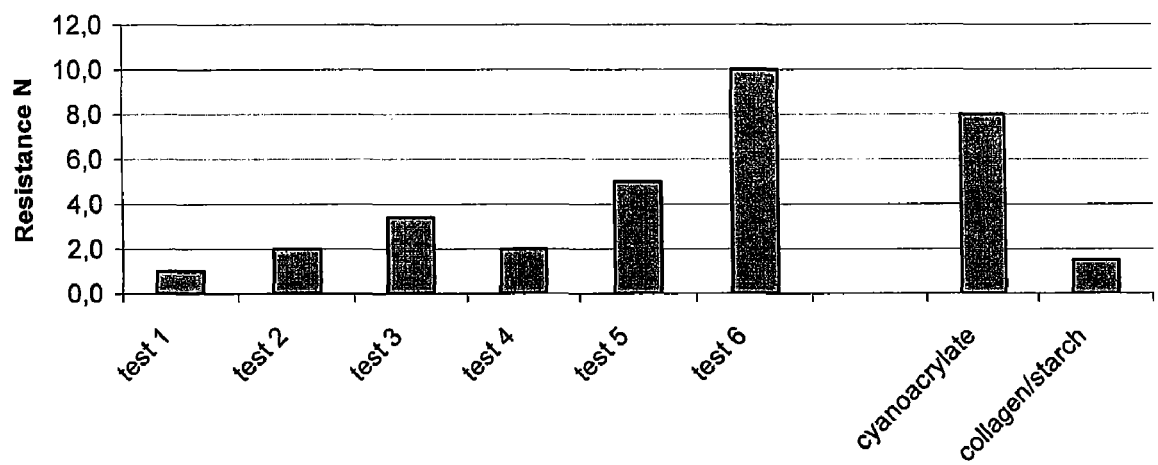

FIGS. 1 and 2: Bond strength (resistance in N) at 2 hours and 20 hours for different glues:
sample 1 (collagen);
sample 2 according to the invention (collagen+glutaraldehyde);
sample 3 according to the invention (collagen+oxidized starch);
sample 4 according to the invention (collagen modified by grafting);
sample 5 according to the invention (collagen modified by grafting+resorcinol);
sample 6 according to the invention (collagen modified by oxidation+resorcinol);
cyanoacrylate glue;
glue made of a solution of collagen and oxidized starch;
fibrin-based glue.

DETAILED DESCRIPTION

On a separate page at the end of the specification, kindly add the Abstract of the Disclosure as presented on the next page:

Undenatured collagen at 0.7%, extracted from calf's skin, is treated according to the following indications:

sample No. 1: the lyophilised collagen with no other treatment is irradiated with β rays at a dose of 20 kGy.

sample No. 2: a solution of glutaraldehyde at 20 mmol/L is added by mechanical stirring to the collagen in suspension so as to obtain in the end 3,500 ppm of aldehyde functions in relation to the collagen. The mixture obtained is poured into cells and lyophilised for 48 h at a final vacuum of less than 0.5 mbars. The product is then irradiated with β rays at a dose of 20 kGy.

sample No. 3: a solution of oxidized starch at 3% (containing approximately 300 μmole of aldehyde functions/g of solution) is added by mechanical stirring to the collagen at a collagen/starch volume ratio of 20:1. The mixture obtained is poured into cells and lyophilised for 48 h at a final vacuum of less than 0.5 mbars. The product is then irradiated with β rays at a dose of 20 kGy.

sample No. 4: to ensure grafting, a glutaraldehyde solution that has been protected by coupling with aminoacetaldehyde is added by mechanical stirring at neutral pH to the collagen in the form of a suspension. After homogenisation for 1 h and three successive strippings to eliminate residual reagents, the solution is acidified to a pH of 3.5. The mixture obtained is poured into cells and lyophilised for 48 h at a final vacuum of less than 0.5 mbars. The product is then irradiated with γ rays at a dose of 25 kGy.

sample No. 5: similar to test 4, adding 0.07% resorcinol in final concentration, in the solution before lyophilisation. The product is irradiated with γ rays at a dose of 25 kGy.

sample No. 6: the collagen at 2% is oxidized using a periodic acid solution at 5 mM for 3 hours at 22° C. The collagen, precipitated in a saline medium, is stripped to eliminate the residual periodic acid and then partially dried with acetone. The fibres obtained are used to form a 0.7% gel to which 0.07% resorcinol is added at the end. The mixture obtained is poured into cells and lyophilised for 48 h at a final vacuum of less than 0.5 mbars. The product is then irradiated with γ rays at a dose of 25 kGy.

During these different tests, the glue is combined in the lyophilisation step with a polyester prosthesis used for wall reinforcement. It should be pointed out that the sterilisation of the samples containing partially crosslinked collagen (samples 2 and 3), performed at 20 kGy or 25 kGy, by β or γ radiation, has no impact on the levels of bonding obtained.

In order to evaluate the effectiveness of the invention, it was compared with implantable glues used in surgery. Three glues representative of three different glue families were chosen as controls:
- fibrin-based glue;
- glue made of a collagen solution and an oxidized starch solution;
- non-implantable cyanoacrylate glue.

The products undergo a bonding test. This test consists in placing the prosthesis coated with the glue between two pieces of muscle imbibed with pH 7 buffer. These are then incubated at 37° C. in a moist medium to recreate the conditions of the system implanted internally.

After 2 and 20 hours of incubation, the samples are subjected to transversal traction and the maximum resistance of the bond is recorded using a dynamometer. The results obtained are presented in table 1 below and illustrated in FIGS. 1 and 2.

TABLE 1

| | Bond strength of the treated collagen | | | |
|---|---|---|---|---|
| | Partial crosslinking | Lyophilisation and sterilisation | Bond strength at 2h (N) | Bond strength at 20h (N) |
| 1 | Collagen alone | + | 2 | 1 |
| 2 | glutaraldehyde | + | 3 | 2 |
| 3 | Oxidized starch | + | 8.0 | 3 |
| 4 | grafting | + | 3.9 | 2 |
| 5 | grafting + resorcinol | + | 5.0 | 5 |
| 6 | oxidation + resorcinol | + | 5.9 | 10 |

We can see that, whatever the alternative used in the context of the invention (tests 2 to 6), the bond strength is greater than non-modified, non-crosslinked collagen (test 1) even after γ ray sterilisation.

The bond strengths obtained with the systems claimed are identical to, or even better than, for fibrin glue and collagen/starch. Test 6 has the highest bond strength, even greater than that of cyanoacrylate glue.

The use of a lyophilised form is advantageous when the bond strength in test 3 is compared with a similar liquid formulation (collagen/starch control). It also initially reinforces the adhesion strength to the muscle. Thus, the lyophilised tests demonstrate a bond strength greater than the controls in liquid form after 2 h.

The use of resorcinol increases bond strength, as can be seen in the comparison of tests 4 and 5. It notably stabilises bond strength over time. Thus, unlike tests 2 to 4, the strengths obtained at 20 h for tests with resorcinol (tests 5 and 6) are greater than or equal to those obtained at 2 h.

The invention claimed is:

1. Glue for gluing two biological tissues together or for gluing a prosthesis onto a biological tissue, said glue comprising:
   a dry, solid lyophilized acidic mixture comprising:
   (i) collagen and a crosslinking agent comprising molecules with at least one aldehyde function, wherein said collagen in said mixture is incompletely crosslinked so that the aldehyde functions remain free to react in situ, or
   (ii) collagen modified to have aldehyde functions, wherein the modified collagen in said mixture is incompletely crosslinked so that the aldehyde functions remain free to react in situ, wherein said dry, solid lyophilized acidic mixture is effective as a glue for gluing two biological tissues together or for gluing a prosthesis onto a biological tissue.

2. Glue as claimed in claim 1, wherein the crosslinking agent is glutaraldehyde.

3. Glue as claimed in claim 1, wherein the crosslinking agent is a biodegradable macromolecular polyaldehyde, oxidized polysaccharide or mucopolysaccharide of natural origin.

4. Glue as claimed in claim 3, wherein the crosslinking agent is oxidized starch.

5. Glue as claimed in claim 1, wherein the modified collagen has aldehyde functions in lysine residues.

6. Glue as claimed in claim 5, wherein the collagen is modified by grafting aldehyde functions or by enzyme reaction.

7. Glue as claimed in claim 1, wherein the modified collagen has aldehyde functions in lysine residues and sugars.

8. Glue as claimed in claim 7, wherein the collagen is modified by oxidative cleavage.

9. Glue as claimed in claim 1, also further comprising at least one phenol.

10. Process for preparing a glue as claimed in claim 1, comprising the following steps:
 forming an acidic mixure comprising:
  (i) collagen and a crosslinking agent comprising molecules with at least one aldehyde function, wherein said collagen in said mixture is incompletely crosslinked so that the aldehyde functions remain free to react in situ, or
  (ii) collagen modified to have aldehyde functions, wherein the modified collagen in said mixture is incompletely crosslinked so that one aldehyde functions remain free to react in situ, and
 lyophilizing said acidic mixture, thereby forming the glue, said glue being suited for gluing two biological tissues together or for gluing a prosthesis onto a biological tissue.

11. Process as claimed in claim 10, wherein the collagen is modified by oxidative cleavage, the oxidative cleavage being achieved by collagen acid solution incubation at ambient temperature, in the presence of a periodic acid solution or one of its salts, at a concentration between 1 and $10^{-5}$ M.

12. Process as claimed in claim 10, wherein said acidic mixture has a pH between 3 and 5.5.

13. Process as claimed in claim 10, further comprising: sterilizing said glue.

14. Process as claimed in claim 10, wherein said collagen is modified to contain 5 to 2,000 µmol of aldehyde functions per gram of collagen.

15. Adhesive prosthesis comprising a prosthetic material combined with a glue as claimed in claim 1.

16. Prosthesis as claimed in claim 15, further comprising on one surface an anti-adherent film made of crosslinked, functionalised hyaluronic acid.

17. Method for preparing an adhesive lyophilized prosthesis comprising the following steps:
 forming an acidic mixture a comprising:
  (i) collagen and a crosslinking agent comprising molecules with at least one aldehyde function, wherein said collagen in said mixture is incompletely crosslinked so that the aldehyde functions remain free to react in situ, or
  (ii) collagen modified to have aldehyde functions, wherein the modified collagen in said mixture is incompletely crosslinked so that the aldehyde functions remain free to react in situ;
 pouring the acidic mixture onto a prosthetic material; and
 lyophilizing the prosthetic material bearing the acidic mixture, thereby forming said adhesive prosthesis.

18. Method for preparing a prosthesis as claimed in claim 17 wherein the crosslinking agent is glutaraldehyde or a biodegradable macromolecular polyaldehyde oxidized polysaccharide or mucopolysaccharide of natural origin.

19. Method for preparing a prosthesis as claimed in claim 17 wherein the collagen is modified by grafting aldehyde functions by enzyme reaction or by oxidative cleavage.

20. Method for preparing a prosthesis as claimed in claim 17, wherein at least one phenol is added to the acidic mixture before said pouring.

21. Method as claimed in claim 17, further comprising:
 coating the prosthesis on one surface with a crosslinked, functionalised hyaluronic acid gel and drying to form a film, and optionally lyophilizing and/or baking the prosthesis.

22. Method as claimed in claim 17, further comprising:
 in a later step, sterilizing the prosthesis.

23. Glue as claimed in claim 9, wherein the at least one phenol comprises resorcinol.

24. Method as claimed in claim 18, wherein the cross linking agent comprises oxidized starch.

25. Method as claimed in claim 20, wherein said at least one phenol comprises resorcinol.

26. Glue according to claim 1 in the form of a sponge or a powder.

27. Glue according to claim 1, wherein said acidified mixture has a pH between 3 and 5.5.

28. Process as claimed in claim 13, wherein said sterilizing comprises:
 exposing said glue to β or γ radiation.

29. Method as claimed in claim 22, wherein said sterilizing comprises:
 exposing said prosthesis to β or γ radiation.

\* \* \* \* \*